(12) United States Patent
Muni

(10) Patent No.: US 6,708,822 B1
(45) Date of Patent: Mar. 23, 2004

(54) COMPOSITIONS AND KITS FOR COMPOUNDING PHARMACEUTICALS

(75) Inventor: Indu A. Muni, North Reading, MA (US)

(73) Assignee: CutisPharma, Inc., Beverly, MA (US)

( * ) Notice: Subject to any disclaimer, the term of this patent is extended or adjusted under 35 U.S.C. 154(b) by 0 days.

(21) Appl. No.: 09/707,783

(22) Filed: Nov. 7, 2000

Related U.S. Application Data

(60) Provisional application No. 60/168,168, filed on Nov. 30, 1999.

(51) Int. Cl.$^7$ .............................. A61J 1/00; A61K 31/00
(52) U.S. Cl. .................. 206/438; 206/538; 206/539; 206/568; 206/570; 206/828; 514/179
(58) Field of Search ................ 206/538, 539, 206/438, 568, 570, 828; 514/179

(56) References Cited

U.S. PATENT DOCUMENTS

| | | | | | |
|---|---|---|---|---|---|
| 4,255,415 A | * | 3/1981 | Chrai et al. | ............ | 424/78 |
| 4,307,555 A | | 12/1981 | Mlodozeniec et al. | ......... | 53/53 |
| 4,332,789 A | | 6/1982 | Mlodozeniec | ............... | 424/27 |
| 4,399,128 A | | 8/1983 | Hirsbrunner | ............... | 424/230 |
| 4,444,310 A | | 4/1984 | Odell | ............ | 206/366 |
| 4,722,733 A | | 2/1988 | Howson | ............. | 604/411 |
| 4,738,956 A | * | 4/1988 | Scott et al. | ............ | 514/179 |
| 4,844,246 A | | 7/1989 | Harrison et al. | ............ | 206/223 |
| 5,014,851 A | | 5/1991 | Wick | ............ | 206/539 |
| 5,040,699 A | | 8/1991 | Gangemi | ............ | 222/1 |
| 5,171,214 A | | 12/1992 | Kolber et al. | ............ | 604/82 |
| 5,538,732 A | | 7/1996 | Smith et al. | ............. | 424/402 |
| 5,563,153 A | | 10/1996 | Mueller et al. | ............. | 514/305 |
| 5,585,398 A | | 12/1996 | Ernst | ............ | 514/537 |
| 5,593,041 A | | 1/1997 | Capozzi | ............ | 206/784 |
| 5,733,886 A | | 3/1998 | Baroody et al. | ............. | 514/24 |
| 5,942,543 A | | 8/1999 | Ernst | ............ | 514/537 |
| 6,489,346 B1 | * | 12/2002 | Phillips | ............ | 514/338 |

OTHER PUBLICATIONS

Bailey, "Phonophoresis with Hydrocortisone 10% in a Highly Visous Complant Base", *International Journal of Pharmaceutical Compounding*.*

Davis, J., "Compounding for Creatures: What Works", *Int'l J. of Pharm. Compounding*, 3(3):182–183 (1999).

"About Compounding:The Art and Skill of Pharmacy Compounding", http://iacprx.org/about_compounding.htm 2 pages.

Bailey, K., "Phonophoresis with Hydrocortisone 10% in a Highly Viscous Complant Base", *Int'l. J. of Pharm. Compounding*, 2(2):110 (1998).

Heckman, H.E., "Problems with Third–Party Payments for Compounded Prescriptions", *Int'l J. Pharm. Compounding*, 2(2):134–136 (1998).

Compounding Legally, Good Compounding Practices:Appendix C.1 *Professional Compounding Center of America Catalogue*, 1998–2000, Houston, TX.

Cumulative Index, *Int'l J. of Pharm. Compounding*, 3(2):166–167 (1999).

* cited by examiner

*Primary Examiner*—S. Mark Clardy
(74) *Attorney, Agent, or Firm*—Wolf, Greenfield & Sacks, P.C.

(57) ABSTRACT

The invention provides compositions and methods for the convenient compounding of pharmaceuticals. Single and multiple unit of use kits are provided which contain all the necessary components required for preparing a compounded pharmaceutical.

45 Claims, 8 Drawing Sheets

COMPOSITIONS AND KITS FOR COMPOUNDING PHARMACEUTICALS

RELATED APPLICATIONS

This application claims priority under 35 U.S.C. §119(e) to U.S. Provisional Patent Application serial No. 60/168,168, filed Nov. 30, 1999 entitled "COMPOSITIONS AND KITS FOR COMPOUNDING PHARMACEUTICALS".

FIELD OF INVENTION

The present invention relates generally to compositions and methods for providing unit-of-use compounded prescriptions.

BACKGROUND OF THE INVENTION

Compounding of pharmaceuticals in its broadest sense refers to the preparation, mixing, assembling, packaging and/or labeling of a drug or device usually resulting from a prescription order from a physician. Under current Food and Drug Administration (FDA) regulations, a qualified pharmacist or a qualified physician can compound a valid prescription for medical or therapeutic use provided the prescription is unsolicited, the pharmacist or physician compounds only one prescription at a time, the patient for whom the prescription is meant is identified, and only FDA acceptable components are used to fill the prescription.

In order to compound and dispense a prescription, particularly a topical formulation, the pharmacist or physician first weighs the different components, for example solids or semi-solids, separately and then mixes solid drug components with a prescribed base, for example a gel, ointment or cream. At present, several vendors such as Paddock Labs, Spectrum and Gallipot sell individual components including active drugs, bases such as gels, ointments, creams, as well as other accessories such as handling equipment, in bulk to qualified pharmacists or physicians for compounding purposes. Typically, a pharmacist or physician buys these components individually in small quantities, not wanting to accrue a large 'expiry date' inventory. Pharmacists or physicians are not allowed by law to compound pharmaceuticals in large quantities, although the anticipatory preparation of limited quantities of a compounded pharmaceutical prior to the submission of a prescription is allowed if such preparation is based on observed regular prescribing patterns. While many of the individual components used in compounding are readily available, the final compounded formulations have not been FDA approved and thus are not currently commercially available.

The process of pharmaceutical compounding is both time-consuming and labor-intensive, especially in comparison to the more common practice of dispensing pre-formulated pharmaceuticals. The preparation of a compounded formulation takes, on average, between 20–30 minutes to complete. In contrast, non-compounded pharmaceutical prescriptions can be filled in a matter of minutes. Technical difficulties also make compounding a less than preferred practice. As an example, for many prescriptions, particularly those for topical use, achieving a uniform suspension between active agent and base is not always guaranteed, thereby reducing the efficacy of the final pharmaceutical product. The maintenance of a clean work environment with accurate instruments for measuring of components, usually necessitating the designation of an area for the sole purpose of compounding, is an additional burden for the compounding pharmacist. Moreover, there is a continual risk (and the associated liability) of error in the measurement of solid or liquid components in the compounding of pharmaceuticals, particularly if the pharmacist is rushed.

As well as being cumbersome, the compounding of pharmaceuticals, in most instances, is not profitable under the current system of health-care reimbursement. This is particularly true if the compounded formulation contains several different components, each of which is identified with an FDA-issued national drug code (NDC) number. Since most health insurance providers, including HMOs, PPOs, Medicare and other federal and state agencies, pay for only one, or at best two, NDC-identified components, compounding pharmacists are not being reimbursed for even the raw cost of the pharmaceutical being dispensed, not to mention the labor costs involved. It is not surprising then that the process of compounding pharmaceuticals has become less desirable for a pharmacist, leading to the current climate in which few if any of the major chain pharmacies provide compounding pharmaceutical service.

SUMMARY OF THE INVENTION

The invention, in part, stems from the realization that there exists a need for a convenient method for preparing accurate and efficacious compounded pharmaceutical formulations. Such a method would undoubtedly be amenable to most pharmacists, resulting in an increased availability of compounded pharmaceuticals to patients. The invention provides compositions for the preparation of compounded pharmaceuticals, as well as methods for their use. In particular, in one aspect, the invention provides a kit comprising the pharmaceutical and handling elements required for producing a compounded pharmaceutical formulation. The kits of the invention contain pre-measured amounts of active and inactive (e.g., base) agents for the preparation and filling of single or multiple prescriptions, and are thus referred to as 'unit-of-use' kits.

In one aspect, the invention provides a kit for compounding pharmaceuticals. The kit comprises a first container comprising an active agent, a second container comprising at least one inactive agent, and instructions for use. The active agent and the at least one inactive agent each is pre-measured into a respective unit of use amount. The at least one inactive agent occupies a volume in the second container equal to or less than the volume of the container minus the volume of the active agent. A mixture of the active agent and the at least one inactive agent is a compounded pharmaceutical selected from the group consisting of testosterone and petrolatum, hydrocortisone and ultrasound gel or ultrasound lotion, triamcinolone and coal tar, ketoprofen and PLO (i.e., pluronic lecithin organo) gel, progesterone and cream, progesterone and PLO gel, testosterone and cream, testosterone and ointment, promethazine and PLO gel, diclofenac and PLO gel, scopolamine and PLO gel, estrogen in lactose, estrogen and progesterone in lactose, MAALOX® (magnesium hydroxide/aluminum hydroxide) and BENADRYL® (diphenhydramine hydrochloride), MAALOX® (magnesium hydroxide/aluminum hydroxide), BENADRYL® (diphenhydramine hydrochloride) and nystatin, and MAALOX® (magnesium hydroxide/aluminum hydroxide), BENADRYL® (diphenhydramine hydrochloride), lidocaine-HCl and lidocaine, adrenaline and tetracaine (i.e., LAT). As used herein, the terms "adrenaline" and "epinephrine" are used interchangeably and thus the "LAT" combination is used interchangeably with the "LET" combination.

The invention intends in one embodiment that the active and inactive agents are physically mixed by a pharmacist to produce a compounded pharmaceutical composition. In other embodiments, the inactive agents are pre-mixed with the active agents and it is the mixture of the active agents which constitutes a compounded pharmaceutical. It is intended that the compounded compositions and the compounding methods of the invention be performed by either a qualified pharmacist or a qualified physician. Thus, as used herein, when reference is made to a pharmacist, a pharmacist and a physician are intended.

In one embodiment, the first and second containers and the instructions may be housed in a package. In another embodiment, the kit contains a mixing element. The first container may also contain an inactive agent selected from the group consisting of a suspending agent and an anti-foaming agent. Preferably, the inactive agent in the first container is not a base inactive agent. The second container preferably contains an inactive agent selected from the group consisting of a base such as a gel or a lotion, a cream, or an ointment, and a liquid base. In some embodiments, the second container also contains a suspending agent, an anti-foaming agent, or both.

In another embodiment, the at least one inactive agent is an anti-foaming agent. In a preferred embodiment, the anti-foaming agent is simethicone.

In yet another embodiment, the at least one inactive agent is a suspending agent. Preferably the suspending agent is propylene glycol.

In one embodiment, the kit comprises an active agent which is testosterone and an inactive agent which is petrolatum. In a preferred embodiment, the compounded pharmaceutical is 2% testosterone in petrolatum.

In another embodiment, the kit comprises an active agent in the form of hydrocortisone and an inactive agent in the form of an ultrasound gel or lotion. Preferably, the compounded pharmaceutical is 10% hydrocortisone in ultrasound gel or lotion.

In still another embodiment, the kit contains two active agents. The kit may contain triamcinolone and coal tar as active agents. In a preferred embodiment, the compounded pharmaceutical is 0.1% triamcinolone with 10% coal tar. In this latter embodiment, coal tar is also an inactive agent.

In still a further embodiment, the kit contains ketoprofen as the active agent and PLO gel as the inactive agent. Preferably, the compounded pharmaceutical is 10% or 20% (in the range of 2–20%) ketoprofen in PLO gel.

In yet a further embodiment, the kit contains three or more active agents. The active agents in these latter embodiments may be estrone, estradiol and progesterone, or estriol, estrone, estradiol and progesterone, or lidocaine, adrenaline and tetracaine (i.e., LAT). The inactive agent in these estrogen containing kits may be lactose. In variations of these latter embodiments, the progesterone may also be omitted such that the kits comprise estrogens alone as active agents.

The invention, in still other embodiments, provides kits which contain PLO as the at least one inactive agent. Such kits contain scopolamine or promethazine as the active agent. In one such embodiment, the compounded pharmaceutical is 5% scopolamine in PLO gel. In another such embodiment, the compounded pharmaceutical is 5% promethazine in PLO gel.

In another embodiment, the invention provides a kit for compounding pharmaceuticals comprising a plurality of containers each housing an active agent pre-mixed with at least one inactive agent and instructions for use. Some such kits may also include a package into which the plurality of containers and the instructions are housed. Each active agent is pre-measured into a respective unit of use amount. The mixture of the active agents is a compounded pharmaceutical.

In yet another embodiment, the kit contains two or more active agents. In a related embodiment, the kit may also contain an inactive agent but it is not so limited. In one embodiment, the active agents of the kit are BENADRYL® (diphenhydramine hydrochloride) and MAALOX® (magnesium hydroxide/aluminum hydroxide). In still further embodiments, the kit contains other active agents, such as lidocaine HCl or nystatin. And in yet other embodiments, the active agents are lidocaine, adrenaline and tetracaine.

In another aspect, the invention provides a kit for compounding pharmaceuticals comprising a first container comprising a first active agent, a second container comprising a second active agent, and instructions for use. The first active agent and second active agent each is pre-measured into a respective unit of use amount, and the first active agent occupies a volume in the first container equal to or less than the volume of the container minus the volume of the second active agent. In one embodiment, a mixture of the first active agent and the second active agent is a compounded pharmaceutical selected from the group consisting of estrogen and progesterone and MAALOX® (magnesium hydroxide/aluminum hydroxide) and BENADRYL® (diphenhydramine hydrochloride). In another embodiment, the kit further comprises a third active agent. In a related embodiment, a mixture of the first active agent, the second active agent and the third active agent is a compounded pharmaceutical selected from the group consisting of MAALOX® (magnesium hydroxide/aluminum hydroxide) and BENADRYL® (diphenhydramine hydrochloride) and nystatin, MAALOX® (magnesium hydroxide/aluminum hydroxide) and BENADRYL® (diphenhydramine hydrochloride) and lidocaine-HCl, and lidocaine, adrenaline and tetracaine (LAT). In one embodiment, the third active agent is housed in a container separate from the first and second containers.

In still other embodiments, the kit comprises a packaging housing the first container, the second container and the instructions for use.

The invention in another aspect provides a method for preparing a compounded pharmaceutical. The method is comprised of physically mixing the active and inactive agents contained within a kit of the invention. For kits which contain only active agents, the method involves physical mixing of the active agents.

DETAILED DESCRIPTION OF THE INVENTION

Figure 1A:
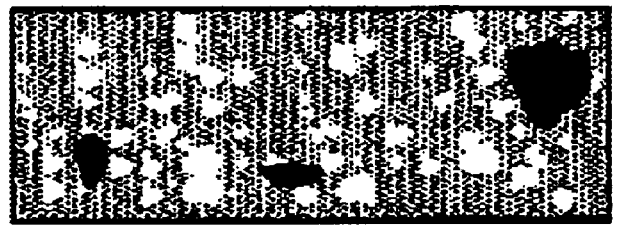
FIG. 1A is a representation of a microscopic analysis of a typical 10% hydrocortisone preparation made according to current conventional compounding practice.

The present invention is directed to compositions and methods useful in the compounding of pharmaceuticals. A compounded pharmaceutical generally is a combination of at least one active agent and at least one inactive agent, preferably in the form of a base agent, although in some instances it is also a combination of two or more active agents. Compounded pharmaceuticals are not available from a pharmacist as a pre-formulated composition. Rather, a compounded pharmaceutical is usually prepared upon receipt of a prescription from a physician for a particular patient. Both the active agent and the inactive agent are commercially available, and either FDA approved or accepted. However, the combination of these agents (i.e., the compounded pharmaceutical) is not FDA approved, nor can it be manufactured in large scale under normal circumstances. Instead, pharmacists usually compound small quantities of these pharmaceuticals for the purpose of filling single prescriptions.

Compounding of pharmaceuticals, in the traditional manner in which it is currently carried out, is laborious and thus the service is not provided by all pharmacists. The invention aims to facilitate the compounding of pharmaceuticals by most pharmacies by providing kits which contain all the necessary components and equipment necessary to prepare with ease a unit of use dose. The term 'single unit of use' as used herein refers to the amount of compounded pharmaceutical required to fill one prescription for one individual. Generally most prescriptions provide enough medication to last for a couple of weeks to a month. As used herein, the term 'medication' refers to a pharmaceutical either in compounded or non-compounded form. Therefore, a unit of use kit would contain a pre-measured amount of each component sufficient to prepare enough of a compounded pharmaceutical to last for a period of time, as specified by the prescribing physician. Each kit will be ascribed a separate NDC number, thereby allowing compounding pharmacists to charge and re-coup the fair reimbursement value of the individual components. In this way, the compounding of pharmaceuticals will no longer be viewed as a non-profitable enterprise, more pharmacists will practice the science of compounding and compounded pharmaceuticals will be more readily available to the average consumer.

The invention also embraces multiple unit of use kits. A multiple unit of use kit refers to a kit which contains sufficient quantities of each required component to fill multiple prescriptions. Pharmacists are allowed to compound pharmaceuticals in quantities greater than that required for a single prescription provided they can present evidence of such customer demand. This latter proviso ensures that the formulation, after having been compounded, is used in short order and is therefore fully efficacious at the time of use. Thus, if a pharmacist has previously experienced a constant, steady and predictable demand for a compounded formulation such as hydrocortisone in an ultrasound gel for example, rather than compounding from a single unit of use kit, the pharmacist may choose to compound from a multiple unit of use kit once a week and dispense this compounded formulation throughout the week. Multiple unit of use kits may contain a vast range of compounding amounts including but not limited to sufficient amounts for preparing 2, 3, 4, 5, 6, 7, 8, 9, 10, 11, 12, 13, 14, 15, 16, 17, 18, 19, 20, 21, 22, 23, 24, 25, 30, 31, 32, 33, 34, 35, 40, 45 and 50 units of use. Multiple unit of use kits are expected to be most practical for hydrocortisone compounded formulations, given the frequent demand for these pharmaceuticals.

The compounded pharmaceuticals embraced by the invention include but are not limited to progesterone topical cream or gel; progesterone capsules; double or triple estrogen capsules (with or without progesterone); testosterone topical cream or ointment; promethazine topical gel; hydrocortisone topical gel for phonophoresis; diaper rash ointment with zinc oxide; ketoprofen topical gel; modified Dakins solution; scopolamine topical gel; BENADRYL® (diphenhydramine hydrochloride) and MAALOX® (magnesium hydroxide/aluminum hydroxide) combination; BENADRYL® (diphenhydramine hydrochloride), MAALOX® (magnesium hydroxide/aluminum hydroxide) and lidocaine combination; BENADRYL® (diphenhydramine hydrochloride), MAALOX® (magnesium hydroxide/aluminum hydroxide) and nystatin combination; progesterone suppositories; triamcinolone acetonide with coal tar; and lidocaine, adrenaline and tetracaine (i.e., LAT).

An important class of compounded pharmaceuticals intended to be provided by the kits of the invention is that used in hormone replacement therapy (HRT). There are many types and forms of hormone replacement therapy available to aging women. Typically, these compounded formulations comprise a combination of one or more estrogens and one progesterone. The importance of individualized therapy and the physician-pharmacist-patient relationship in providing optimal HRT is well documented. Rather than prescribing a very limited number of FDA approved HRT products, physicians are choosing and selecting various natural hormone combinations for post-menopausal women. Based upon family history and present health of a patient, a 30 day supply of Triest (i.e., three estrogen combination) or Biest (i.e., two estrogen combination) regimen with or without progesterone is commonly prescribed. Triest includes a mixture of estriol, estradiol, and estrone while Biest contains estriol and estradiol. Pre-weighed mixtures of these natural hormones which are all commercially available and FDA accepted, along with pre-weighed diluent (e.g., lactose) would easily be supplied in a typical 30-day unit of use kit.

The kits of the invention will contain at least one active agent. The active agent may be a pharmaceutical which is commonly available over the counter, such as for example, the combination of magnesium hydroxide and aluminum hydroxide which is commercially sold as MAALOX® (magnesium hydroxide/aluminum hydroxide). Alternatively, the active agent may be a pharmaceutical which is only available by prescription from a physician, such as hydrocortisone. The active agent may also be a scheduled drug as determined by the United States Drug Enforcement Agency (USDEA or DEA). An example of a scheduled drug is testosterone. As used herein the terms 'component' and 'agent' are used interchangeably to refer to the compounds housed within the kit which when combined result in a compounded pharmaceutical. In some embodiments, the kits of the invention will contain two or more active agents.

Examples of active agents useful in the invention include testosterone, hydrocortisone, triamcinolone, ketoprofen, progesterone, estrogen with or without progesterone, MAALOX® (magnesium hydroxide/aluminum hydroxide), BENADRYL® (diphenhydramine hydrochloride), zinc oxide, promethazine and scopolamine, lidocaine, adrenaline and tetracaine and diclofenac, but are not so limited. As used herein, testosterone refers to testosterone or any salts thereof including but not limited to testosterone propionate or testosterone cypionate. In a similar fashion, hydrocortisone refers to hydrocortisone or any salts thereof including but not limited to hydrocortisone acetate and hydrocortisone phosphate. Other active agents for the purposes of the invention are anesthetics such as lidocaine HCl, or antifungal agents such as nystatin. When coal tar is used, it may act as either or both an active and an inactive agent.

Active agents can be provided in kits in variable amounts depending on the kit and the particular ailment they are intended to treat. The active agents of the invention are preferably administered in therapeutically effective amounts. As used herein, an "effective amount" of the compounded pharmaceutical of the invention is that dosage sufficient to produce a medically desirable effect. A therapeutically effective amount is not, however, a dosage so large as to cause adverse side effects. Generally, a therapeutically effective amount may vary with the subject's age, condition, and sex, as well as the extent of the disease in the subject and can be determined by one of skill in the art. The dosage of currently compounded pharmaceuticals may be adjusted by the individual physician in the event of any complication. A therapeutically effective amount typically will vary from about 0.01 mg/kg to about 500 mg/kg, more typically from about 0.1 mg/kg to about 200 mg/kg, and even more typically from about 0.2 mg/kg to about 20 mg/kg, in one or more dose administrations daily, for one or several days (depending, of course, on the mode of administration and the factors discussed above).

As an example, hydrocortisone may be present in amounts which yield 0.5%–25% (w/w) hydrocortisone in the final compounded product. In preferred embodiments, the range of hydrocortisone in the final compounded pharmaceutical is 1%–15%. Even more preferably, the range of hydrocortisone in the final compounded pharmaceutical is 5%–10%. Similarly, in testosterone containing kits, the amount of testosterone provided will depend on the nature of each particular kit and its intended use. Testosterone may be provided in quantities sufficient for producing a 0.1%–10% (w/w) final testosterone concentration. In preferred embodiments, the final testosterone concentration will be 0.5%–5%. In even more preferred embodiments, the final testosterone concentration will be 0.5%–2%. For all stipulated ranges, it is intended that the concentration of the agent in the final compounded formulations can be the ends of the range as well as every integer therebetween as if each had been specifically mentioned herein.

Active components can be present in solid, semi-solid or liquid form. Solid forms include for example, powders, granules and flakes. Semi-solid forms include, for example, gels, creams, gelatins and ointments. These and other active agents embraced by the present invention are known to those of ordinary skill in the art and, in most cases, are commercially available from suppliers such as Paddock Laboratories and Gallipot. Information on these and other active and inactive agents embraced by the invention, and their commercial suppliers is available from various trade manuals, most particularly, Remington's Pharmaceutical Sciences, United States Pharmacopoeia (USP), National Formulary (NF), Merck Index, Physician's Desk Reference (PDR) and Chemical Abstracts.

The kits of the invention will also generally contain at least one inactive agent. As used herein, inactive agents are agents which do not provide any therapeutic benefit to the subject to whom they are administered. Instead, inactive agents can function in many other ways such as to provide a base in which the active agent can be dissolved or suspended, to dilute the active agent in order to provide proper doses upon administration, to facilitate the dissolution or suspension of the active agent, or to prevent oxidation of the active agent by removing air bubbles from the final compounded suspension. In some embodiments of the invention, the kits lack an inactive agent, and rather contain two or more active agents.

Base agents such as creams, oils, gels or ointments are suitable for topical or suppository applications. The choice of suitable inactive base agent for use in the kits of the invention will depend upon the active agent to be compounded. Suitable base agents will be known to the ordinary artisan. Alternatively, Remington's Pharmaceutical Sciences, the Physician Desk Reference (PDR) or other manuals as listed above, can be consulted in making this determination.

Examples of inactive base agents or components include, for example, lanolin, hydrophilic ointment, white ointment, yellow ointment, polyethylene glycol ointment, petrolatum, hydrophilic petrolatum, white petrolatum, rose water ointment, squalene, hydrogenated vegetable oil (Type II), ultrasound gel, pluronic lecithin organogel (PLO) gel, cream and coal tar. As described herein, coal tar may function in some compounded pharmaceuticals as both active or inactive agent. Alternatively, coal tar may function as an active in one compounded formulation and as an inactive in another compounded formulation.

The term 'petrolatum' as used herein means petrolatum ointment, petrolatum gel or petrolatum cream, all of which are commercially available. It is well within the realm of the ordinary pharmaceutical artisan to determine which form of petrolatum is most appropriate for a specific kit.

A commercially available ultrasound base is either POLYSONIC® (ultrasound gel) ultrasound lotion or Aquasonic ultrasound 100 gel manufactured by Parker Laboratories, Inc. (Fairfield, N.J.) or EcoGel 100 or EcoGel 200 manufactured by Eco-Med (Mississauga, Ontario, Canada), the compositions of which may include cetyl alcohol, liquid paraffin, polymer, surfactants, preservatives such as propyl paraben and methyl paraben in bacteriostatic concentration, fragrance, and reverse osmosis water. As used herein, a gel is a base with a higher viscosity than a lotion. The physical characteristics of the POLYSONIC® (ultrasound gel) ultrasound lotion and the EcoGel 100 include pH range of 6.5–7.0, density of 1.04 g/cm$^3$, viscosity of 35,000 to 70,000 cps and acoustic impedence of 1.60 ($10^5$ g/cm$^2$ sec). The physical characteristics of Aquasonic ultrasound 100 gel or EcoGel 200 are similar to those of POLYSONIC® (ultrasound gel) ultrasound lotion and Eco-Gel 100 except that their viscosity is 80,000 to 110,000 cps. These lotions and gels are available in a clear, colorless form or in a blue colored form. In some embodiments, the blue form is preferred.

Liquid bases are recommended for orally administered pharmaceuticals. In some embodiments of the invention, at least one active agent will be supplied already co-mingled with an inactive agent. Examples of this include the combination of magnesium hydroxide and aluminum hydroxide (commercially available as MAALOX® (magnesium hydroxide/aluminum hydroxide)), and diphenhydramine HCl (commercially available as BENADRYL® (diphenhydramine hydrochloride)). Both MAALOX(® (magnesium hydroxide/aluminum hydroxide) and BENADRYL® (diphenhydramine hydrochloride) are supplied by their respective manufacturers as a combination of active and inactive agents. The compounded pharmaceutical embraced by the invention is the combination of MAALOX® (magnesium hydroxide/aluminum hydroxide) and BENADRYL® (diphenhydramine hydrochloride). This combination will contain both active and inactive agents due to the presence of inactive agents in the pre-formulated individual components. The combination of MAALOX® (magnesium hydroxide/aluminum hydroxide) and BENADRYL® (diphenhydramine hydrochloride) can be further supplemented with other active agents such as lidocaine HCl or nystatin to produce other compounded pharmaceuticals.

Sterile base solutions are preferred for parenteral (i.e., injection), aerosol (i.e., inhalation) and ophthalmic routes of administration. The administration may, for example, be intravenous, intraperitoneal, intramuscular, intracavity, subcutaneous or transdermal. Preparations for parenteral administration includes sterile aqueous or nonaqueous solutions, suspensions and emulsions. The compounded pharmaceuticals, preferably those intended for parenteral, inhalation or ophthalmic routes of administration, may be prepared and administered in inactive agents which are pharmaceutically-acceptable. As used herein, a pharmaceutically-acceptable carrier means a non-toxic material that does not interfere with the effectiveness of the biological activity of the active agents and that is compatible with the biological systems such of a tissue or organism. The physiologically acceptable carrier must be sterile for in vivo administration. Pharmaceutically acceptable carriers include diluents, fillers, salts, buffers, stabilizers, solubilizers and other materials which are well-known in the art. The characteristics of the carrier will depend on the route of administration. In general, pharmaceutically-acceptable agents or carriers are well-known to those of ordinary skill in the art. In important embodiments, suitable sterile solutions include albuterol and ipratropium inhalation solution; papaverine, phentolamine and prostaglandin injection solution; fentanyl citrate injection solution and cyclosporine ophthalmic drops.

Examples of nonaqueous solvents are propylene glycol, polyethylene glycol, vegetable oil such as olive oil, an injectable organic esters such as ethyloliate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, (such as those based on Ringer's dextrose), and the like. Preservatives and other additives may also be present such as, for example, antimicrobials, antioxidants, chelating agents, and inert gases and the like. Those of skill in the art can readily determine the various parameters for preparing these alternative pharmaceutical compositions without resort to undue experimentation.

Inactive agents may also include components which function to preserve the integrity of the compounded formulation. This latter category of inactive agents includes, for example, anti-foaming agents. Anti-foaming agents are agents which function to remove unwanted air trapped in a composition, perhaps during mixing or agitation. The use of anti-foaming components is particularly useful in the preparation of pharmaceuticals to be used for ultrasound imaging due to the impedance of signal transmission by air bubbles. Examples of other anti-foaming agents useful in the compositions of the invention include bisphenylhexamethicone, dimethicone, dimethiconol, hexamethyldisiloxane, hexyl alcohol, isopropyl alcohol, petroleum distillates, phenethyl disiloxane, phenyl trimethicone, polysilicone-7, propyl alcohol, silica dimethyl silylate, silica silylate, tetramethyl decynediol and trimethylsiloxysilicate. A preferred anti-foaming agent is simethicone. Simethicone is a mixture of about 90% dimethicone and 10% silicone dioxide (w/w). Simethicone is used extensively as an anti-gas agent in pharmaceutical products such as GAS-X® (simethicone), MAALOX® (magnesium hydroxide/aluminum hydroxide), MYLANTA® (aluminum, magnesium simethicone), PHAZYME® (simethicone), GENAZYME® (simethicone), and MYLICON® (simethicone) Drops. Simethicone may be used as an anti-foaming agent in any of the formulations embraced by the invention.

Other inactive agents which can be included in the formulations of the invention include stabilizers such as citric acid, anti-oxidants such as sodium metabisulfite and preservatives such as methyl or propyl paraben.

Another class of inactive agents is suspending agents. Suspending agents are agents which facilitate the suspension and in some cases the dissolution of an active agent in a base. Generally, suspending agents ensure more uniform mixing of active and base components. In order to administer a more uniform dose of a compounded pharmaceutical to a patient, the compounded components must be properly and homogeneously combined. If the active agent is present as a powder, a uniform dispersion is sometimes difficult to achieve using the traditional form of compounding.

A subcategory of suspending agents are solubilizers. Solubilizers are agents which facilitate the dissolution of a solid or, in some cases, a semi-solid agent in a base inactive agent. In some embodiments of the invention, a solid-form active agent may be dissolved in a suspending agent, prior to mixing it with the base agent. Conversely, the suspending agent and the base agent may be prepackaged together, particularly if the concern is ensuring the uniform blending of active agent within the base component rather than the loss of solid (i.e., powdery) active agent. In still other variations, the suspending agent may be premixed with the base inactive agent.

Suitable suspending agents useful in the compositions of the invention include, but are not limited to, glycerin, hexylene glycol, propylene glycol, sorbitol, acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monstearate, stearic acid, trolamine, emulsifying wax, benzalkonium chloride, benzethonium chloride, cetylpyridinium chloride, docusate sodium, nonoxynol 9, nonoxynol 10, octoxynol 9, polyoxyl 50 stearate, and tyloxapol.

Still other suspending agents include humectants and wetting agents. Humectants are agents which retain moisture. Examples of humectants include but are not limited to glycerin, hexylene glycol, propylene glycol and sorbitol.

The amounts of base and non-base inactive agents will also depend upon the particular compounded pharmaceutical to be made. Base agents can be provided in quantities corresponding to final compounded preparations which contain 0.5% to 99.99% of base agent, either in weight or in volume. In preferred embodiments, the final concentration of the base agent is 20%–80%. In even more preferred embodiments, the final concentration of the base agent is 40%–80%.

Generally, the amounts of non-base agents will be sufficient to provide final formulations in which each non-base inactive agent represents 0.01%–50% (w/w) of the composition. Suspending agents may represent 1%–50% (w/w) of the final formulation. Preferably, suspending agents will represent 1%–40% and even more preferably, they will represent 5%–30% of the final formulation. Anti-foaming agents may represent 0.01% to 20% (w/w) of the final formulation. More preferably, anti-foaming agents represent 0.05% to 10% of the final formulation and even more preferably, they represent 0.1% to 5% of the final formulation.

Although the invention provides for a number of active and inactive agents, only specific combinations of these are intended in the preparation of a compounded pharmaceutical. That is to say, the afore-mentioned active agents are not meant to be randomly combined with the afore-mentioned inactive agents, nor are the afore-mentioned active agents intended to be randomly combined with other afore-mentioned active agents. Rather, only specific combinations are desired, including but not limited to for example the combination of testosterone with petrolatum, hydrocortisone with ultrasound gel, triamcinolone with coal tar and ketoprofen with PLO gel.

In some preferred embodiments, the single or multiple unit of use kits are designed to yield, after the physical mixing of active and inactive agents, compounded pharmaceutical formulations with for example the following compositions: 2% (weight by volume) testosterone in petrolatum, 10% (w/v) hydrocortisone in ultrasound gel, 0.1% (w/v) triamcinolone in 10% (w/v) coal tar, 10% or 20% (w/v) ketoprofen in PLO gel. Coal tar is routinely supplied by manufacturers as a 20% (w/v) composition. Thus, when a physician prescribes a 10% coal tar formulation, he or she usually intends that the final formulation be composed of 10% (v/v) of the stock (i.e., 20%) solution of coal tar. In effect, the physicians are prescribing a 2% coal tar formulation but regarding it as 10%. As provided in the kits of the invention, coal tar will be pre-measured to reflect 10% (v/v) of the final formulation.

The suspending agent and the anti-foaming agent can be housed together, and thus added together to the active component, prior to mixing with the base agent. Alternatively, at least one inactive agent may be pre-mixed with at least one of the active agents. As yet another alternative, the suspending agent and/or the anti-foaming agent can be premixed with a base agent. And in yet another example, the suspending agent and/or the anti-foaming agent can be premixed with the active agent.

The kits of the invention will provide each and every component required for preparing a given compounded pharmaceutical in pre-measured quantities. The measuring of each component will be performed using current Good Manufacturing Practices (cGMP, as legislated by the Code of Federal Regulations or CFR), as will the packaging and labeling of each component and the final packaging and labeling of the kit in its entirety. In this way, the kits are standardized and variations from batch to batch will be minimal or non-existent and the precision and accuracy in the measurement of individual components will be improved considerably over the methods currently used by pharmacists. Instructions may be provided as separate from any container, but still contained in the kit. Alternatively, instructions may be located on a container, for example, on an exterior surface or on an interior surface such as a lid.

Figure 3A:
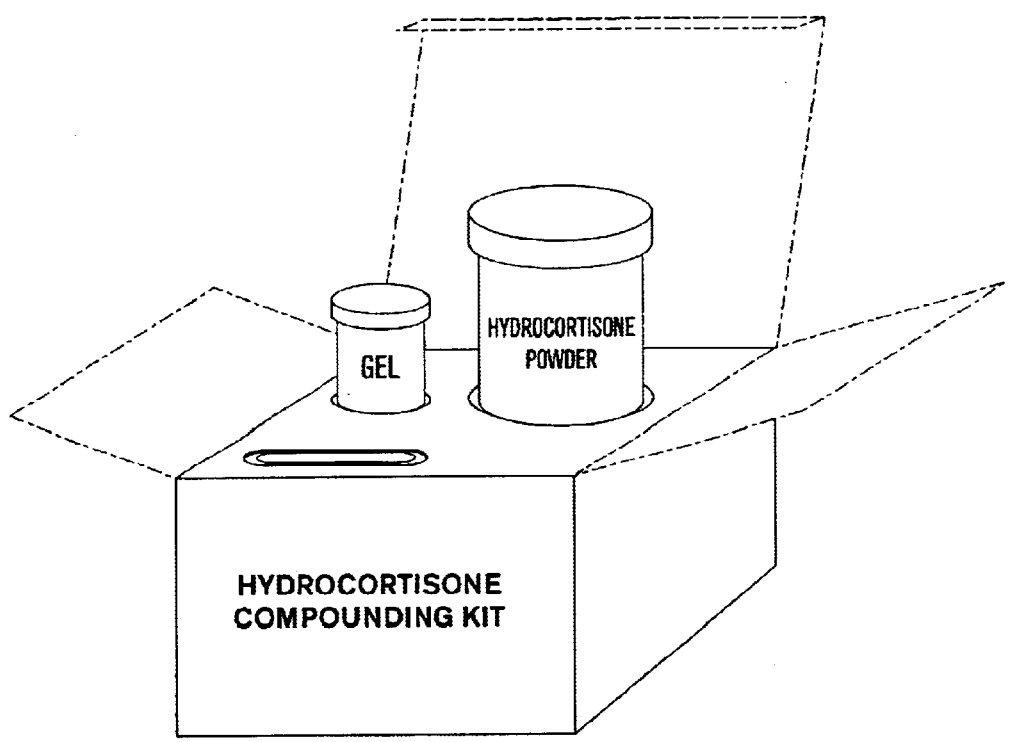
FIG. 3A is a representative diagram of a FIRxST® unit of use compounding kit for hydrocortisone in an ultrasound gel, including hydrocortisone powder suspended in propylene glycol and simethicone in one container (e.g., a plastic or glass jar) and an ultrasound gel in a second container (e.g., a plastic vial or tube or jar or a pouch), and a mixing element such as a rod or a spatula made out of wood, plastic, metal or glass.
Figure 3B:
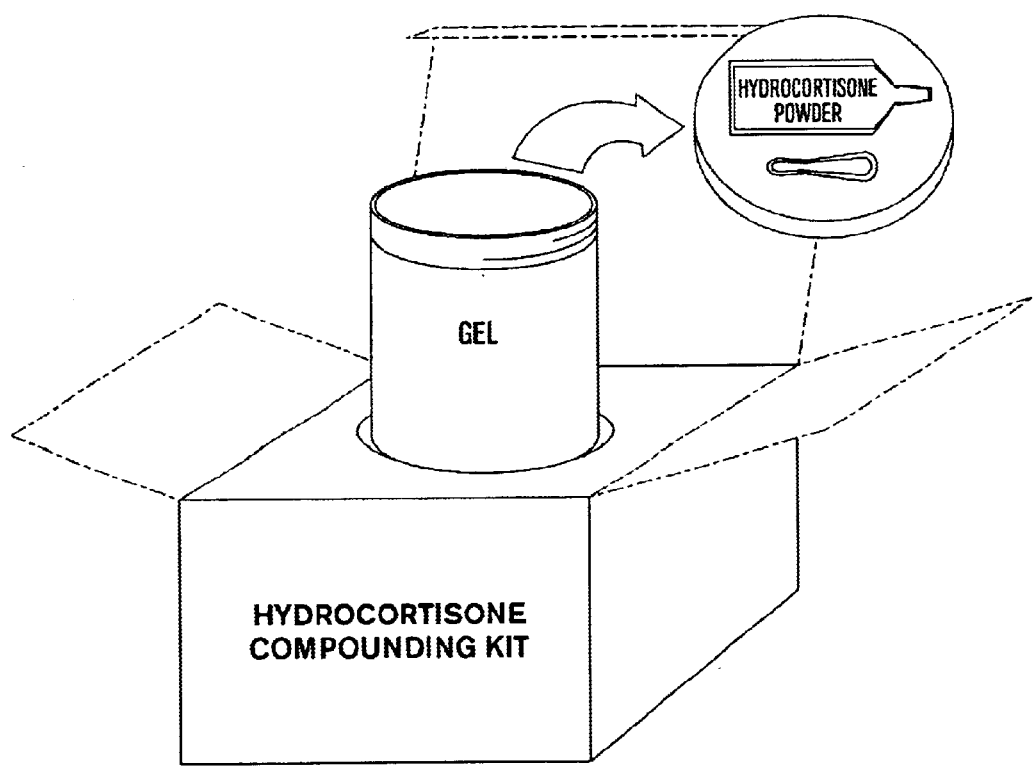
FIG. 3B is a representative diagram of FIRxST® unit of use compounding kit for hydrocortisone in an ultrasound gel, including hydrocortisone powder, propylene glycol and simethicone in, for example, a plastic tube or a pouch attached to the lid of a container (e.g., a jar) containing an ultrasound gel, and a mixing element such as a glass rod or a spatula (e.g., also attached to the lid of the jar containing the ultrasound gel).
Figure 3C:
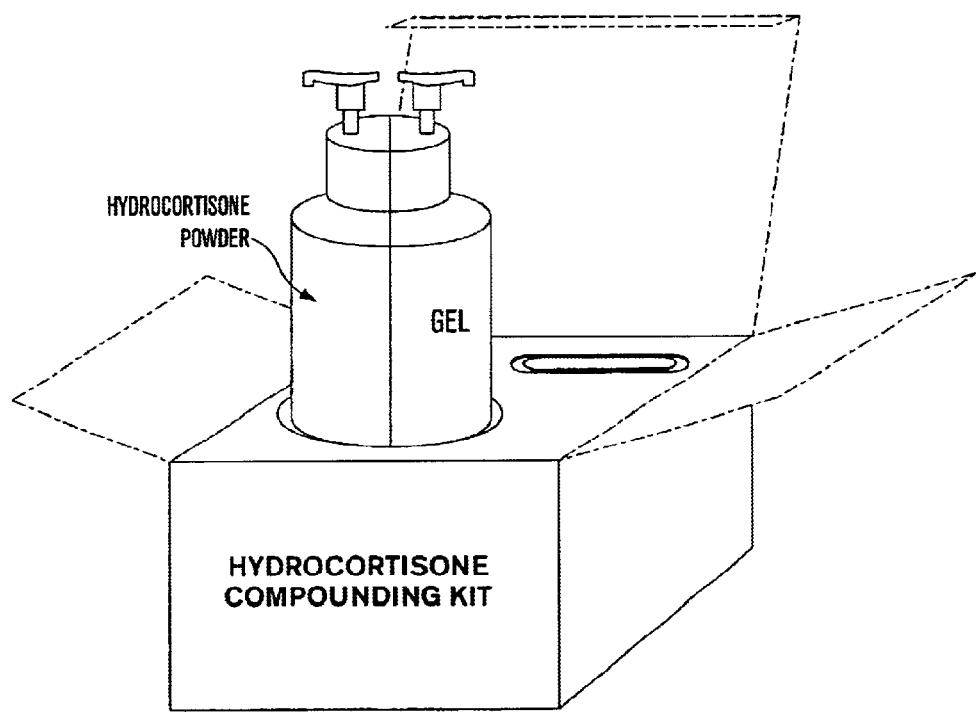
FIG. 3C is a representative diagram of a FIRxST® unit of use compounding kit for hydrocortisone in an ultrasound gel, including hydrocortisone powder, propylene glycol and simethicone in one chamber of a container (e.g., a pump with two dispensing tubes), and an ultrasound gel in another, separate chamber of the same container, and a mixing element such as a glass rod or a spatula.
Figure 4:
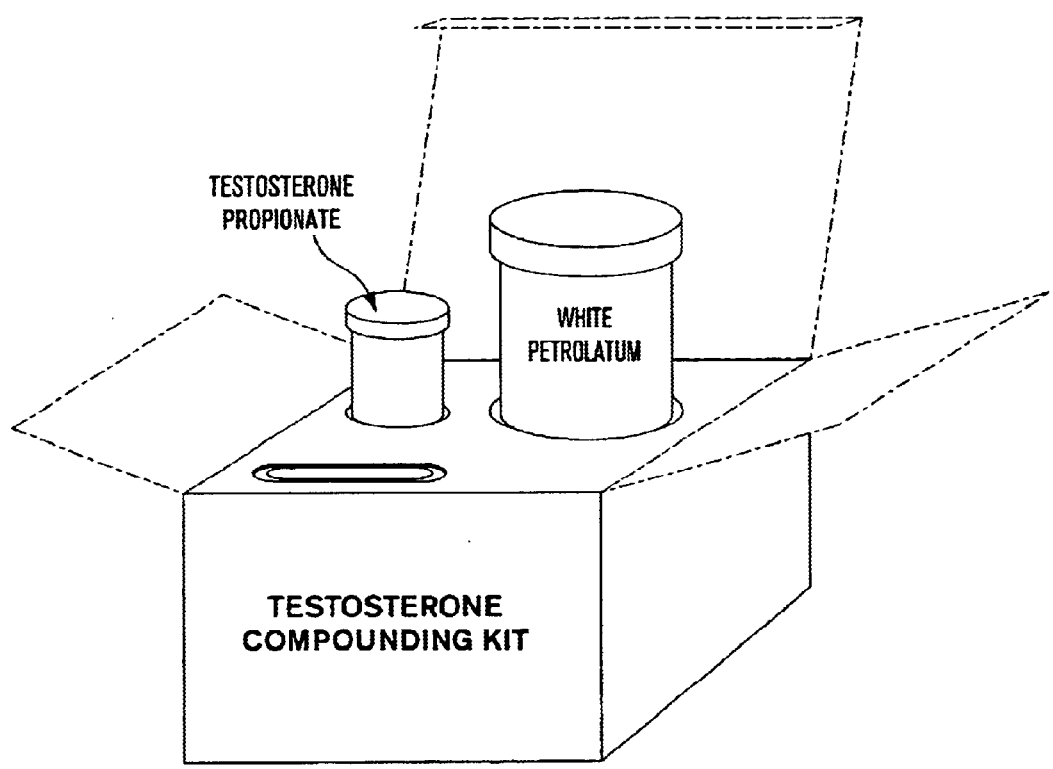
FIG. 4 is a representative diagram of a FIRxST® unit of use compounding kit for testosterone in petrolatum, including testosterone propionate in sesame oil with preservatives (e.g., benzyl alcohol) and anti-oxidants (e.g., BHT) in a container (e.g., a glass or plastic vial or tube or a jar or a pouch), petrolatum gel in another container (e.g., a plastic or glass jar) and a mixing element such as a wood, plastic, metal or glass spatula or rod.
Figure 5:
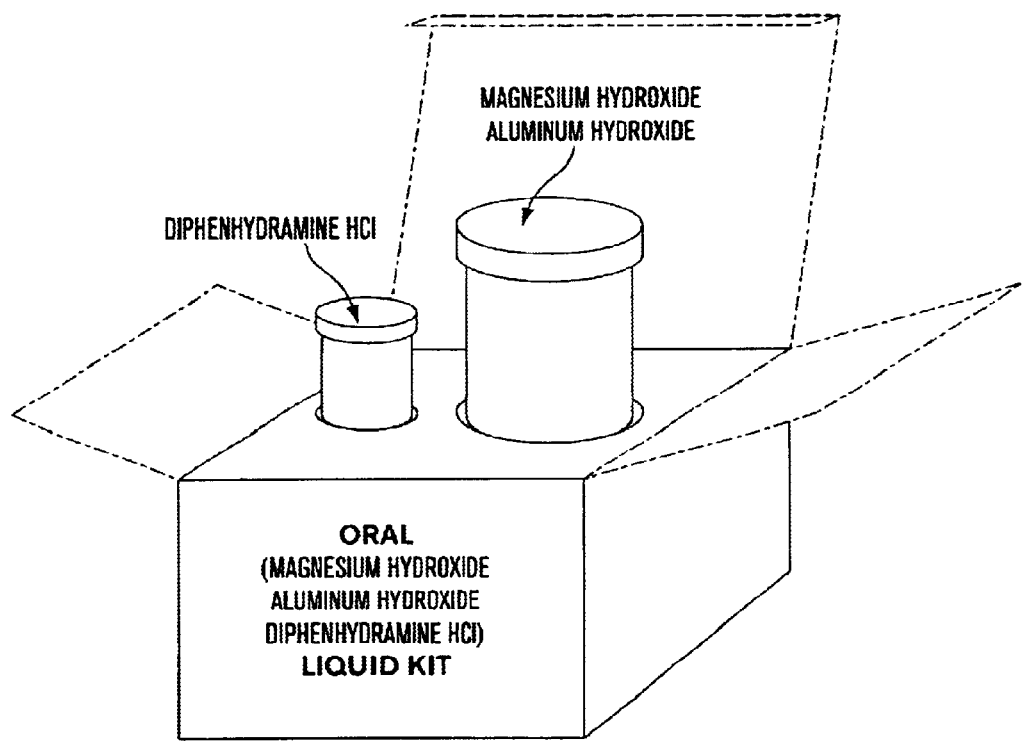
FIG. 5 is a representative diagram of a FIRxST® unit of use oral compounding kit for magnesium hydroxide with aluminum hydroxide and diphenhydramine-HCl comprising diphenhydramine-HCl in one container and magnesium hydroxide with aluminum hydroxide in a separate container.
Figure 6:
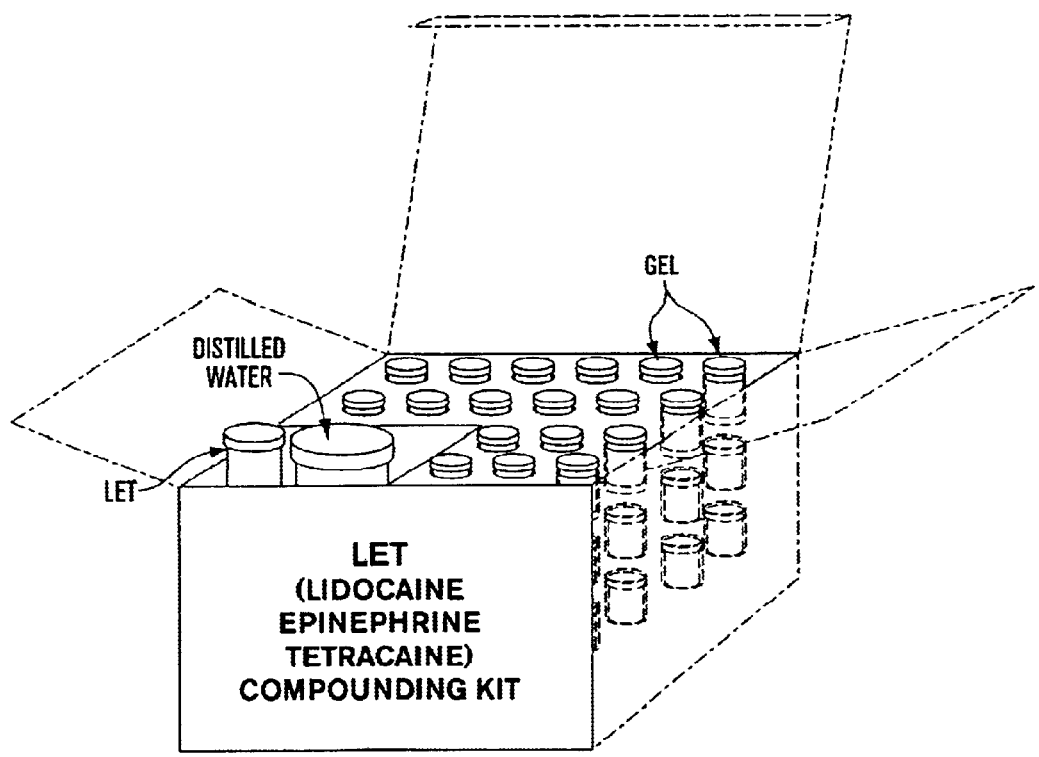
FIG. 6 is a representative diagram of a FIRxST® unit of use compounding kit for lidocaine, adrenaline and tetracaine with lidocaine, adrenaline, tetracaine, sodium metabisulfite and optionally citric acid in one container and acidified distilled water and optionally methyl and/or propyl paraben in another container. The kit further contains a plurality of vials (possibly arranged in one or more layers) containing a derivative of cellulose for the purpose of forming a gel for the topical administration of the LAT formulation.

Both the active and the inactive agents of the kit are provided in containers. Since the kit will contain at least one active and at least one inactive agent, or at least two active agents pre-formulated with inactive agents, the minimum number of containers in a given kit will be two. In preferred embodiments, the maximum number of containers in a kit will be less than or equal to four. The containers may be formed in any size or shape useful for the mixing or transferring of components from one container to another. For example, each container may be in the form of vials, bottles, squeeze bottles, jars, sealed sleeves, envelopes or pouches, tubes or blister packages or any other suitable form provided the container is sealed so as to prevent premature mixing of components. As used herein, a container may also be a compartment or a chamber within a vial, a tube, ajar, or an envelope, or a sleeve, or a blister package or a bottle, provided that the contents of one compartment are not able to associate physically with the contents of another compartment prior to their deliberate mixing by a pharmacist or physician. Examples of suitable packaging of components are shown in FIGS. 3, 4 and 5.

The invention intends to provide within a single kit all the necessary components, containers and stirring or mixing elements for preparing a unit of use compounded pharmaceutical without the need for other accessories. The kits of the invention may also contain items such as gloves or spill pads. Individuals skilled in the art can readily modify the choice of container to suit the individual components housed and mixed therein.

In some embodiments of the invention, the final compounded formulation will be provided to the patient in the container originally housing the inactive, or base, compound. In other embodiments, the final compounded formulation will be provided in the container originally housing the active agent. An example of this is shown in FIG. 3A. In still other embodiments, all the necessary components for preparing a compounded pharmaceutical are included in one container but are physically separated within such a container. For example, an inactive agent may be contained in the lower part of a container, such as a jar, and may be covered by a plastic, peel-off wrap. The active agent may be housed in this same jar, but secured to the lid of the jar and provided in a pouch or a sleeve. The ability to provide all components together in the smallest packaging arrangement may be preferable in some circumstances. Mixing elements required in the preparation of the compounded pharmaceutical may also be located within the same container, for example, secured to the inside surface of the lid of the container.

In still another embodiment of the invention, active and inactive agents are provided in adjacent compartments of a single housing container, and are mechanically removed from these compartments and into a third compartment. As an example, all the chemical components necessary to prepare a particular compounded pharmaceutical can be present in a single tube, for example, a tube similar to a toothpaste tube having an interior which is divided into separate compartments. Each of these compartments in turn house a base agent or an active agent. Either the base agent or the active agent may be premixed with an anti-foaming agent and/or a suspending agent, as described herein. By applying pressure on the tube as a whole, the components are made to exit their respective compartments. They can then be mixed either in an adjacent or a physically separate compartment. Squeezing or pressing of the outside surface of the tube may be all that is necessary to retrieve the individual components housed within the tube. In yet another embodiment, the contents of both chambers of a container can be pumped out and into a third container. This latter embodiment is illustrated in FIG. 3C. In a related embodiment, it is also envisioned that rather than requiring the contents of each compartment to exit and flow into a third compartment, the components may be separated by a removable sheet or film. Thus, upon removal of such a sheet or film, the contents of the two compartments are in contact and may require only agitation or end-over-end inversion to become completely mixed. This latter embodiment would eliminate the need for a mixing element, and potentially for an exterior package particularly if the instructions are written on the container itself.

According to some aspects of the invention, each container may contain one or more active agents or one or more inactive agents. For example, in some embodiments of the invention, none of the containers may contain both an active and an inactive agent prior to mixing by the pharmacist or physician. However, the invention also provides for kits in which a container may contain an active and at least one inactive agent, such as a base agent, a suspending agent or an anti-foaming agent. For example, since hydrocortisone, prior to compounding, is usually commercially available as a cream, a container housing hydrocortisone or its salts may already contain an active agent and an inactive (i.e., base) agent. Similarly, testosterone is commercially available as a pre-mixture of testosterone, oil, benzyl alcohol which acts as a preservative, and butylated hydroxytoluene (BHT) which acts as an anti-oxidant. In other embodiments, the active agent may be provided premixed with an inactive agent. This latter instance may exist if the active agent is commercially available as a solid, for example a powder, and the pre-mixing of the powder with a suspending agent facilitates the compounding by the pharmacist or physician. In yet other embodiments, at least two of the inactive agents may be pre-mixed as provided in the kits of the invention.

In some embodiments, where the active agent is added to the base component, it may be desirable to provide the base component in a container which is only partially full. In preferred embodiments, the container in which the base component is situated is less than 100% full by volume. In other embodiments, the containers are 95%, 90%, 80%, 75%, 70%, 60%, 50%, 40%, 30%, 25%, 20% or less than 20% full by volume. In other embodiments, the active or inactive agents comprise a volume of their respective containers ranging from 100% to greater than 1%, and every integer therebetween. In preferred embodiments, the inactive agent occupies a volume of the second container which is less than or equal to the volume of the second container minus the volume of the active agent.

As used according to the invention, the active and inactive agents are physically combined by a pharmacist to produce a compounded pharmaceutical. The components of the kit can be combined by gentle agitation, shaking, stirring, folding or end-over-end inversion of the first or second container. In some instances, the proper mixing of the active and inactive agents may be accomplished simply by adding one to the other, followed by sealing and gentle agitation of the container. This is especially the case if the components are both liquids or both semi-solids. In other instances, it may be necessary to stir the components together with a mixing element. Mixing elements are well known to a person of ordinary skill in the pharmaceutical arts and may include for example, a mixing rod such as a glass rod, a spoon, a spatula or a dipstick. Where required, the mixing element is provided in the kit. The presence of a mixing element will vary depending on the compounded pharmaceutical formulation to be made with the components of a kit.

The final compounded pharmaceutical may be formulated into preparations in solid, semi-solid, liquid or gaseous forms such as tablets, capsules, powders, granules, ointments, solutions, suppositories, inhalants and injections, and usual ways for oral, parenteral or surgical administration. The invention also embraces locally administering the compounded pharmaceuticals of the invention such as, for example, as implants. These formulations may be intended for oral, topical, mucosal, parenteral (e.g., injectable), rectal or vaginal administration. In preferred embodiments, the final compounded formulations may be self-administered.

The kits of the invention may also contain a package which may be compartmentalized to receive in close confinement two or more containers of the invention. In some embodiments, the package may be box-like, being made of a moderately rigid material such as cardboard or reinforced paper. Examples of such packages are shown in FIGS. 3A, 3B, 3C, 4, and 5. In other embodiments, the package may be a bag. In still other embodiments, as described herein, there is no external packaging and all containers may be incorporated into one of the containers housing either an active or an inactive agent. This latter embodiment can be accomplished by securing containers such as pouches, sleeves or sacs, containing either active or inactive agents, as well as any mixing elements required for the compounding, to the interior of the lid of the main container. An example of this is shown in FIG. 3B. An individual skilled in the art can readily modify the package to suit the individual needs of each kit and each use. The kits of the invention further contain instructions for the proper use of the components found therein.

The kits of the invention are intended for use in the treatment or prevention of a number of disorders in a variety of subjects including humans, dogs, cats, horses, fish, pigs, cows, sheep, deer, zoo animals and laboratory animals (e.g., mice, rats, rabbits, monkeys, etc.). Pharmaceutical compounding for veterinary purposes is an important aspect of the present invention. Examples of veterinary compounded pharmaceuticals include potassium bromide capsules, metronidazole suspension of various strengths depending upon the disorder and its severity, methimazole in 5-, 10-, and 100-mg/ml oral form, diethylstilbestrol in 0.5, 1 mg, 2 mg, 3 mg and 5 mg capsules, potassium bromide solution, cyclosporin 2% ophthalmic solution, prednisone in 0.5- 1-, 5-, and 10-mg/ml oral form, amitriptyline in 5- to 100-mg/ml oral form, chloramphenicol in 150 mg/ml oral suspension, and protamine zinc insulin in 10 to 100 units/ml form. The invention intends to embrace unit of use kits containing the above preparations.

The following examples are provided to illustrate specific instances of the practice of the present invention and are not to be construed as limiting the present invention to these examples. As will be apparent to one of ordinary skill in the art, the present invention will find application in a variety of compositions and methods. Importantly, although the following examples provide particular arrangements of component within kits, the invention intends to embrace equivalent arrangements in which components are housed separately or together with one or more other components of the kit.

EXAMPLES

Example 1

FIRxST™ Hydrocortisone in Ultrasound Gel

A compounded pharmaceutical preparation of 10% strength hydrocortisone (e.g., such as that commercially available from Paddock Labs, Spectrum or Gallipot) in an ultrasound gel (e.g., such as that commercially available from Parker Labs or Eco-Med) is routinely prescribed for phonophoresis procedures for the treatment, for example, of acute or sub-acute bursitis, acute or sub-acute tendinitis or osteoarthritis. It is important that the final gel preparation is homogeneous as to the dispersion of hydrocortisone in the gel for uniform applications. It is also desired that the final product has no or minimally trapped air (e.g., in the form of air bubbles) since the ultrasound waves do not transmit through air. In the traditional manner of compounding pharmaceutical, a pharmacist weighs hydrocortisone powder and ultrasound gel separately and then attempts to make a homogeneous suspension by adding the dry powder to the gel and stirring it for several minutes (e.g., 15 to 20 minutes). This results in a final preparation which contains many air bubbles as well as clumps or clusters of the active drug. The kits of the invention have solved the problems of composition uniformity and trapped air by first solubilizing, or softening, hydrocortisone in a mixture of propylene glycol and simethicone, and then adding the gel to the mixture of hydrocortisone, propylene glycol, and simethicone.

Figure 1B:
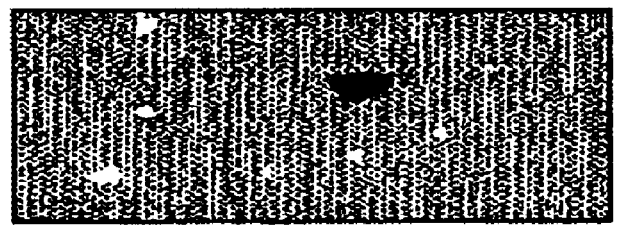
FIG. 1B is a representation of a microscopic analysis of a typical 10% hydrocortisone preparation made using the compounding kit of the invention.
Figure 2A:
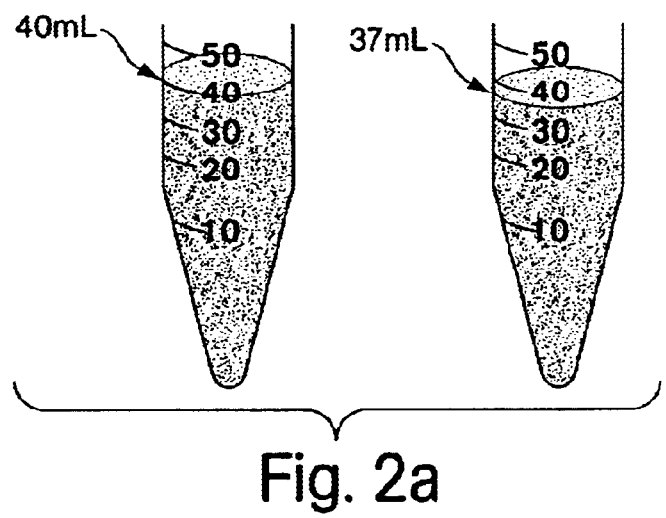
FIG. 2A is a schematic representation of the volume of a typical compounded pharmaceutical made according to current conventional compounding practice, prior to (left panels) and following centrifugation (right panels) to remove trapped air bubbles.
Figure 2B:
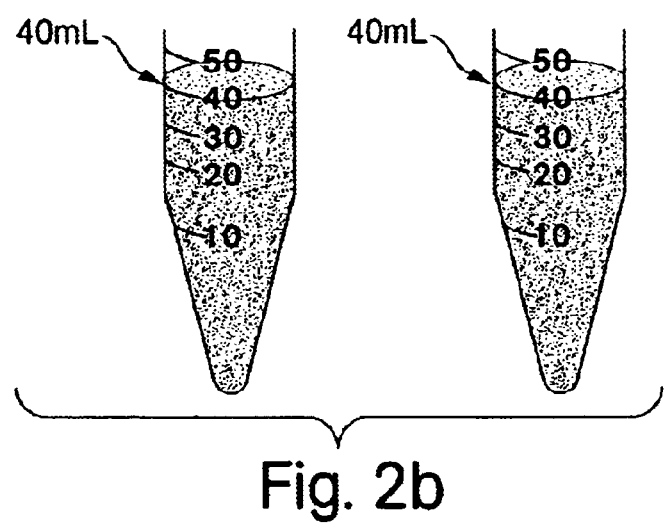
FIG. 2B is a schematic representation of the volume of a typical compounded pharmaceutical made using the compounding kit of the invention, prior to (left panels) and following centrifugation (right panels) to remove trapped air bubbles.

Simethicone, acting as an anti-foaming agent, substantially reduces the number of air bubbles formed during the mixing process. FIGS. 1 and 2 demonstrate the superiority of the compounded pharmaceuticals prepared using the unit of use kits of the invention. A comparison of the final compounded hydrocortisone formulation made using the unit of use kit and conventional compounded procedures is shown in FIGS. 1 and 2. FIG. 1 shows the microscopic analysis of the conventionally prepared hydrocortisone formulation (1A) and the unit of use formulation (1B). Each is a representative result from 10 separately prepared mixtures. After being made, the preparations were sprayed onto a glass microscope slide. The black spots represent air bubbles trapped in the mixture. The white spots represent clumps of undissolved hydrocortisone.

FIG. 2 demonstrates the extent of air trapped into a hydrocortisone formulation prepared conventionally (2A) and using the unit of use kit containing simethicone (2B). The left panel shows the volume of the mixtures prior to centrifuging at 3000 g for 30 minutes. The right panel shows the volume after centrifugation. The decrease in volume in the conventionally prepared formulation demonstrates the propensity of the conventional prior art compounding method to introduce air bubbles into such formulations. On average, the volume of the conventionally prepared formulation dropped by 4–8%, while the volume of the unit of use preparation did not change significantly upon centrifugation.

A typical single unit of use kit may contain 6 gm of hydrocortisone USP, micronized, 18 gm of propylene glycol USP, 60 mg of simethicone USP and 36 gm of an ultrasound gel. Preferably, the hydrocortisone powder is supplied pre-suspended in the suspending agent such as propylene glycol and the anti-foaming agent such as simethicone, and the ultrasound gel is supplied in a separate container. The compounding pharmacist then need only combine the contents of the two containers in order to prepare the compounded pharmaceutical. Alternatively, the kit may contain hydrocortisone separately from either or both the suspending agent and/or the anti-foaming agent, as well as separately from the inactive base agent. In this latter instance, a pharmacist using the kit to prepare hydrocortisone in an ultrasound gel may first add the hydrocortisone provided in the kit to a container housing the combination of a suspending agent such as propylene glycol and an anti-foaming agent such as simethicone and then after brief mixing, add this mixture to the container housing the inactive base agent. By providing pre-measured components, an ideal suspending agent and an anti-foaming agent, the kit format results in a better quality product, while also reducing the preparation time by five-fold over the traditional method.

Example 2

FIRxST® (Unit of Use Compounding Kit) Testosterone in Petrolatum

A 2% testosterone in petrolatum base formulation is commonly prescribed by physicians to treat loss of libido. Testosterone is commercially available as a propionate or cypionate salt in oil (10 ml) in an injectable form. Testosterone is classified as a schedule III drug by the USDEA. In order to compound the required prescription using the traditional method of compounding, a pharmacist must break open the injection vial (i.e., ampoule) and use only a portion of the oil solution for compounding. Although the remaining drug in the opened ampoule may be kept and stored for future use, this is not highly recommended particularly since first, it could never be used for parental administrations, second, its stability in an open environment is not ensured, and third, it is no longer guaranteed to be contamination-free. As an alternative, many pharmacists choose to dispose of the opened ampoules, however this may be costly given that testosterone (and thus its disposal) is regulated by the DEA. Another significant drawback of the present method of compounding testosterone in a petrolatum base is that the mixing of testosterone and petrolatum without other agents invariably results in a non-homogenous suspension in which the testosterone is not significantly dissolved in the petrolatum base. The present invention has addressed these issues by providing pre-measured, single or multiple use kits, such as the FIRxST® (unit of use compounding kit)-Testosterone kit, described herein. A typical testosterone kit might include 1.434 gm of testosterone propionate USP, 120 mg of benzyl alcohol NF, 2.4 mg of butylated hydroxytoluene (BHT) NF, 12 ml sesame oil NF, added to 48 gm of white petrolatum to yield a total weight of 60 g (±10%). Generally, the kit may contain one bottle, one jar (preferably containing the petrolatum) and a stirrer, with the preparation of the formulation requiring the mixture of the contents of the bottle with the contents of the jar followed by gentle stirring for 2–3 minutes until the appearance is homogenous.

Example 3

FIRxST® (Unit of Use Compounding Kit) Ketoprofen in PLO Gel

Ten percent or 20% ketoprofen in PLO (pluronic lecithin organo) gel is prescribed for the treatment of a number of disorders including but not limited to arthritis, osteo-arthritis and rheumatoid arthritis. Approximately 500,000 such prescriptions are filled each year in the United States. The present invention provides a unit of use kit which allows for a one step preparation of ketoprofen in PLO gel formulations. In one embodiment, the kit comprises a premeasured mixture of ketoprofen and alcohol and optionally propylene glycol in one container. The kit further comprises in a separate container a premeasured mixture of lecithin and poloxamer (i.e., PLO gel). The PLO gel may be provided with the appropriate preservatives (e.g., propyl paraben), anti-oxidants (e.g., sodium metabisulfite), fragrances and the like. The ketoprofen/alcohol preparation is expected to have a shelf-life of at least 2 years, therefore the kit itself can have a shelf life of 2 years from the day of manufacture. Prior to the present invention, a compounding professional was required to combine ketoprofen with alcohol with a mortar and pestle, followed by the addition of the lecithin component and the solubilization of the alcohol in the lecithin component. Following this, the poloxamer component is added with vigorous trituration. This process takes approximately 30 minutes. The unit of use kit of the present invention significantly shortens the time required to prepare such a formulation and reduces the likelihood of error in the preparation.

Example 4

FIRxST® (Unit of Use Compounding Kit) LAT (Lidocaine, Adrenaline and Tetracaine)

Of the roughly 22 million emergency room visits by children 15 years of age and younger, approximately 2 million are for the treatment of skin abrasions and lacerations such as facial and scalp lacerations. It is common to use an anesthetic which is a combination of lidocaine, adrenaline and tetracaine (LAT) for the suturing of such wounds. As used herein, the terms "adrenaline" and "epinephrine" are used interchangeably to denote the same compound and accordingly the terms "LAT" and "LET" are used interchangeably also. The LAT combination anesthetic is commonly used due to its ability to act both quickly and to be long-acting. The lidocaine component provides rapid onset of the anesthesia but is generally intermediate acting. The tetracaine component has a slower onset but is longer acting than lidocaine. The epinephrine component provides vasoconstriction, thereby reducing loss of blood in the wound area as well as reducing the toxicity of administered agents because of the reduced blood flow and uptake of the drugs into the circulation.

The unit of use kits provided herein provide LAT formulations in which lidocaine is provided in the range of 1.0–10.0% weight/volume (w/v), epinephrine is provided in the range of 0.01–0.1% w/v, and tetracaine is provided in the range of 0.25–4% w/v. An example of a LAT formulation which is provided by a unit of use kit comprises a 4% lidocaine, 1:1000 epinephrine and 0.5% tetracaine. The formulation may comprise other agents as well such as stabilizers (e.g., citric acid), preservatives (e.g., methyl or propyl paraben), and anti-oxidants (e.g., sodium metabisulfite). The latter formulation can be prepared as follows:

| Lidocaine | Lidocaine HCl, USP | 4,000 mg |
|---|---|---|
| Epinephrine | Epinephrine Bitartrate, USP (55% epinephrine, 45% bitartrate) or | 180 mg |
|  | Epinephrine HCl, USP | 180 mg |
| Tetracaine | Tetracaine HCL, USP | 500 mg |
|  | Sodium Metabisulfite | 75 mg |
|  | Citric Acid | 200 mg |
|  | Methyl and/or Propyl Paraben (optional) |  |
|  | Sterile Water* for Irrigation | 100 ml |

*preferably acidified and distilled

Currently, compounding professionals place powdered ingredients in a graduated cylinder and add water to 100 ml. The unit of use kit provided herein requires that the compounding professional simply open two containers and mix the ingredients. In one preferred embodiment, the kit also contains vials which themselves contain a cellulose derivative such as for example methylcellulose 4000 cps. The mixture of LAT with the aqueous solution is then dispensed into the vials in order to prepare lotion or gel formulations which are suitable for topical administration.

Example 5

FIRxST® (Unit of Use Compounding Kit) Triamcinolone Acetonide with Coal Tar

A 0.1% triamcinolone acetonide cream in 10% coal tar is frequently prescribed by dermatologists for the treatment of, for example, eczema and psoriasis. Coal tar is a mixture of hydrocarbons having a peculiar and unpleasant smell, and is a suspected carcinogen with known toxic fumes. In traditional compounding procedures, pharmacists remove an aliquot of coal tar solution from a reservoir bottle and weigh an accurate quantity of required coal tar for mixing with triamcinolone acetonide. Because of the nature of coal tar, it is impossible to avoid spills during weighing and mixing. Coal tar spills lead to the release of an unpleasant smell and, more importantly, toxic fumes, in the vicinity of the compounding area. In addition, coal tar spills produce stains which are difficult to remove. One of the kits provided by the invention, namely the 0.1% triamcinolone acetonide cream in 10% coal tar, referred to herein as the FIRxST® (unit of use compounding kit)-TACT kit, eliminates the need for aliquoting, weighing and transferring coal tar and thus saves time, unnecessary exposure to toxic material and minimizes spillage.

Example 6

FIRxST® (Unit of Use Compounding Kit)-Oral Liquid Kits

The invention provides kits for compounding of oral pharmaceuticals such as: MAALOX® (magnesium hydroxide 40mg/ml and aluminum hydroxide 45mg/ml) with BENADRYL® (diphenhydramine HCl 2.5mg/ml) 1:1 v/v; MAALOX® (magnesium hydroxide/aluminum hydroxide), BENADRYL® (diphenhydramine hydrochloride) and 2% lidocaine HCl solution 1:1:1 v/v/v; and MAALOX® (magnesium hydroxide/aluminum hydroxide), BENADRYL® (diphenhydramine hydrochloride) and nystatin suspension (100,000 units/ml) 1:1:1 v/v/v. These oral liquid compounded formulations account for approximately 600,000 prescriptions annually. They are frequently prescribed by physicians for the temporary relief from, for example, itching, burning and pain in the oral cavity due to infection or inflammation. These formulations are commonly prescribed by oncologists for patients undergoing cancer chemotherapy, or by physicians treating HIV infected patients exhibiting AIDS related symptoms. The typical prescribed volume is 4 oz (i.e., 118 ml).

While all these drugs are available generically, the unit volumes in which they are provided are much greater than those required for respective compounding needs. Unit of use oral liquid kits improve the accuracy and precision of compounding pharmaceuticals. This, in turn, improves the quality of the products and saves time for the pharmacists. In addition, the kits of the invention (i.e., FIRxST® (unit of use compounding kits) kits) address the very important issue of disposing or storing the excess unused liquid drugs once opened.

Example 7

FIRxST® (Unit of Use Compounding Kit) Hormone Replacement Therapy Kits

As stated above, hormone replacement therapy involves the administration of a combination of two or three forms of estrogen with a progesterone. In one specific example of a Triest single unit of use kit, estriol (2.0 mg), estrone (0.25 mg), estradiol (0.25 mg) and progesterone (100 mg) are combined in a lactose base to provide a 2.5 mg dose. In a typical 30 day unit of use kit of Triest, 60 mg of estriol, 7.5 mg of estrone, 7.5 mg of estradiol and 3 gm of progesterone are supplied along with a lactose base. The ability to provide the patient with aliquots from the same mixture for the 30 day treatment period will undoubtedly reduce the variation in each component administered if the formulation is newly compounded each day.

Example 8

Common Compounded Pharmaceuticals Containing PLO Gel

The PLO containing compounded formulations listed below all contain a lecithin/isopropyl palmitate solution and a poloxamer base. The compositions of these common constituents are as follows:

| Lecithin/Isopropyl Palmitate: | |
|---|---|
| Lecithin NF | 100 gm |
| Isopropyl Palmitate NF | 117 ml |
|  | (100 gm) |
| Sorbic Acid Powder NF | 0.66 gm |
| Total | 220 ml |
| Poloxamer base: | |
| Poloxamer NF | 20 gm |
| Potassium sorbate NF | 0.3 gm |
| Distilled Water | 80 ml |
| Total | 100 ml |

In some preferred embodiments, the kits comprise a container having a premixed PLO gel stored therein, rather than the individual lecithin/isopropyl palmitate and poloxamer base components. The premixed PLO gel may contain soy lecithin, isopropyl palmitate, poloxamer 407, vitamin E, methyl paraben and/or propyl paraben, fragrance and water.

PLO containing formulations include:

| 10% Ketoprofen Topical Gel: | |
|---|---|
| Component A: | |
| Ketoprofen | 6.0 gm |
| Alcohol or | 8.0 ml |
| Alcohol/ | (6–10 ml range) |
| Glycol mixture | |
| Component B: | |
| PLO Gel* | 46 gm |
|  | (44–48 gm range) |
|  | 60 gm total |
| 20% Ketoprofen Topical Gel: | |
| Component A: | |
| Ketoprofen | 12.0 gm |
| Alcohol or | 8.0 ml |
| Alcohol/ | (6–10 ml range) |
| Glycol mixture | |
| Component B: | |
| PLO Gel* | 40 gm |
|  | (38–42 gm range) |
|  | 60 gm total |
| Promethazine Topical Gel: | |
| Component A: | |
| Promethazine HCl, USP | 3.38 gm |
| Water | 2.62 ml |
| Component B: | |
| PLO Gel* | 54.0 gm |
|  | 60 gm total |

*Premixed poloxamer-lecithin organo gel is commercially available from Maxima (Edmonton, Alberta, Canada). It can be supplemented with appropriate anti-oxidant(s), preservative(s), and/or fragrances.

It should be understood that the preceding is merely a detailed description of certain preferred embodiments. It therefore should be apparent to those skilled in the art that various modifications and equivalents can be made without departing from the spirit and scope of the invention. Those skilled in the art will recognize, or be able to ascertain using no more than routine experimentation, many equivalents to the specific embodiments of the invention described herein. Such equivalents are intended to be encompassed by the appended claims. All references, patents and patent publications that are recited in this application are incorporated in their entirety herein by reference.

I claim:

1. A kit for compounding pharmaceuticals comprising:
a first container comprising an active agent,
a second container comprising at least one inactive agent, and
instructions for use,
wherein the active agent and the at least one inactive agent each is pre-measured into a respective unit of use amount,
wherein the at least one inactive agent occupies a volume in the second container equal to or less than the volume of the second container minus the volume of the active agent, and
wherein a mixture of the active agent and the at least one inactive agent comprises a compounded pharmaceutical selected from the group consisting of testosterone and petrolatum, hydrocortisone and ultrasound gel and an anti-foaming agent, triamcinolone and coal tar, ketoprofen and PLO gel, progesterone and cream, progesterone and PLO gel, diclofenac and PLO gel, testosterone and cream, testosterone and ointment, promethazine and PLO gel, scopolamine and PLO gel, estrogen in lactose, estrogen and progesterone in lactose, magnesium hydroxide/aluminum hydroxide and diphenhydramine hydrochloride, magnesium hydroxide/aluminum hydroxide and diphenhydramine hydrochloride and nystatin, magnesium hydroxide/aluminum hydroxide and diphenhydramine hydrochloride and lidocaine-HCl, and lidocaine, adrenaline and tetracaine (LAT), and
wherein the anti-foaming agent is present in an amount of 0.01–10% (w/w).

2. The kit of claim 1, wherein the kit contains a mixing element.

3. The kit of claim 1, wherein the at least one inactive agent is an anti-foaming agent.

4. The kit of claim 3, wherein compounded pharmaceutical contains an anti-foaming agent in an amount selected from the group consisting of 0.01%, 0.05%, 0.1%, 5% and 10% (w/w).

5. The kit of claim 4, wherein the anti-foaming agent is simethicone.

6. The kit of claim 1, wherein the at least one inactive agent is a suspending agent.

7. The kit of claim 6, wherein the suspending agent is propylene glycol.

8. The kit of claim 1, wherein the active agent is testosterone and the at least one inactive agent is petrolatum.

9. The kit of claim 1, wherein the compounded pharmaceutical is 2% testosterone in petrolatum.

10. The kit of claim 1, wherein the active agent is hydrocortisone and the at least one inactive agent is ultrasound gel and an anti-foaming agent.

11. The kit of claim 1, wherein the compounded pharmaceutical is 10% hydrocortisone in ultrasound gel and 0.1–5% anti-foaming agent (w/w).

12. The kit of claim 1, wherein the active agents are triamcinolone and coal tar.

13. The kit of claim 12, wherein the at least one inactive agent is coal tar.

14. The kit of claim 1, wherein the compounded pharmaceutical is 0.1% triamcinolone with 10% coal tar.

15. The kit of claim 1, wherein the active agent is ketoprofen and the at least one inactive agent is PLO gel.

16. The kit of claim 1, wherein the compounded pharmaceutical is 10% ketoprofen in PLO gel.

17. The kit of claim 1, wherein the compounded pharmaceutical is 20% ketoprofen in PLO gel.

18. The kit of claim 1, wherein the active agents are estrone, estradiol and progesterone and the at least one inactive agent is lactose.

19. The kit of claim 1, wherein the active agents are estriol, estrone, estradiol and progesterone and the at least one inactive agent is lactose.

20. The kit of claim 1, wherein the active agent is scopolamine and the at least one inactive agent is PLO gel.

21. The kit of claim 1, wherein the compounded pharmaceutical is 5% scopolamine in PLO gel.

22. The kit of claim 1, wherein the active agent is promethazine and the at least one inactive agent is PLO gel.

23. The kit of claim 1, wherein the compounded pharmaceutical is 5% promethazine in PLO gel.

24. The kit of claim 1, wherein the active agents are diphenhydramine hydrochloride and magnesium hydroxide/aluminum hydroxide.

25. The kit of claim 1, wherein the active agents are diphenhydramine hydrochloride, magnesium hydroxide/aluminum hydroxide and lidocaine HCl.

26. The kit of claim 1, wherein the active agents are diphenhydramine hydrochloride, magnesium hydroxide/aluminum hydroxide and nystatin.

27. The kit of claim 1, wherein the active agents are lidocaine, adrenaline and tetracaine.

28. The kit of claim 1, wherein the active agent is progesterone and the at least one inactive agent is PLO gel.

29. The kit of claim 1, wherein the active agent is diclofenac and the at least one inactive agent is PLO gel.

30. The kit of claim 1, further comprising a package housing the first container and the second container and the instructions.

31. The kit of claim 1, wherein a second inactive agent is present in the first container.

32. The kit of claim 31, further comprising a third inactive agent in the second container.

33. The kit of claim 1, wherein a second inactive agent is present in the second container.

34. The kit of claim 33, further comprising a third inactive agent in the first container.

35. The kit of claim 1, wherein the active agent is testosterone and the at least one inactive agent is cream.

36. The kit of claim 1, wherein the compounded pharmaceutical is 2% testosterone in cream.

37. The kit of claim 1, wherein the active agent is progesterone and the at least one inactive agent is cream.

38. The kit of claim 1, wherein the compounded pharmaceutical is 10% progesterone in cream.

39. The kit of claim 1, wherein the estrogen is selected from the group consisting of one estrogen, a two estrogen combination, and a three estrogen combination.

40. The kit of claim 1, wherein the at least one inactive agent is an alcohol.

41. A kit for compounding pharmaceuticals comprising:
a first container comprising an active agent and optionally comprising a second inactive agent,
a second container comprising at least one inactive agent, and
instructions for use, wherein the active agent and the at least one inactive agent each is pre-measured into a respective unit of use amount, wherein the at least one inactive agent occupies a volume in the second container equal to or less than the volume of the container minus the volume of the active agent, wherein a mixture of the active agent and the at least one inactive agent comprises a compounded pharmaceutical selected from the group consisting of testosterone and petrolatum, hydrocortisone and ultrasound gel and anti-foaming agent, triamcinolone and coal tar, ketoprofen and PLO gel, progesterone and cream, progesterone and PLO gel, diclofenac and PLO gel, testosterone and cream, testosterone and ointment, promethazine and PLO gel, scopolamine and PLO gel, estrogen in lactose, estrogen and progesterone in lactose, magnesium hydroxide/aluminum hydroxide and diphenhydramine hydrochloride, magnesium hydroxide/aluminum hydroxide and diphenhydramine hydrochloride and nystatin, magnesium hydroxide/aluminum hydroxide and diphenhydramine hydrochloride and lidocaine-HCl, and lidocaine, adrenaline and tetracaine (LAT), and the anti-foaming agent is present in an amount of 0.01–10% (w/w).

42. The kit of claim 41, wherein the estrogen is selected from the group consisting of one estrogen, a two estrogen combination, and a three estrogen combination.

43. The kit of claim 41, wherein the compounded pharmaceutical is 10% hydrocortisone in ultrasound gel and 0.1–5% anti-foaming agent (w/w).

44. The kit of claim 41, wherein compounded pharmaceutical contains an anti-foaming agent in an amount selected from the group consisting of 0.01%, 0.05%, 0.1%, 5% and 10% (w/w).

45. The kit of claim 41, wherein the at least one inactive agent is an alcohol.

* * * * *